United States Patent [19]

Buchanan et al.

[11] Patent Number: 5,117,002
[45] Date of Patent: May 26, 1992

[54] PREPARATION OF DIPHENYL ETHER

[75] Inventors: Robert A. Buchanan; Jeffrey S. Stults, both of Grand Island, N.Y.

[73] Assignee: Occidental Chemical Corporation, Niagara Falls, N.Y.

[21] Appl. No.: 640,781

[22] Filed: Jan. 14, 1991

[51] Int. Cl.$^5$ .................. C07D 307/77; C07C 43/225
[52] U.S. Cl. ...................... 549/241; 568/312; 568/433; 568/585; 568/586; 568/635; 568/639; 548/633; 558/420; 560/64; 562/473; 562/886; 562/887
[58] Field of Search ............... 568/585, 586, 635, 639, 568/312, 433; 548/433; 558/420; 560/64; 562/473, 886, 887; 549/241

[56] References Cited

U.S. PATENT DOCUMENTS

| 4,558,164 | 12/1985 | Jones et al. | 568/585 |
| 4,933,469 | 6/1990 | Berhahl et al. | 548/461 |

FOREIGN PATENT DOCUMENTS

| 44-14334 | 6/1969 | Japan | 568/585 |
| 7890230 | 8/1978 | Japan |  |
| 24125 | 2/1980 | Japan | 568/635 |

OTHER PUBLICATIONS

R. L. Markezich & O. S. Zamek J. Org. Chem. vol. 42, 3431 (1977).

*Primary Examiner*—Howard T. Mars
*Attorney, Agent, or Firm*—James F. Tao; Richard D. Fuerle

[57] ABSTRACT

A process for the production of diaryl ethers which comprises heating, to a temperature of 80° C. to 220° C., a compound of the formula

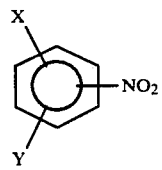

wherein X and Y are selected from the group consisting of H, CN, CO$_2$H, CHO, NO$_2$, and CF$_3$, provided that both X and Y may not simultaneously be H, in a solvent, in the presence of an inorganic base selected from the group consisting of the alkali metal carbonates, bicarbonates, and hydroxides, and in the presence of a catalyst selected from the group consisting of benzoic acid, substituted benzoic acids, C2–C4 aliphatic carboxylic acids, and alkali metal salts of said acids.

32 Claims, No Drawings

PREPARATION OF DIPHENYL ETHER

BACKGROUND OF THE INVENTION

This invention relates to a process for the preparation of nitro-substituted diphenyl ethers from aromatic nitro compounds. The nitro-substituted diphenyl ethers are useful intermediates for the synthesis of amino-substituted diphenyl ethers which are useful as intermediates for the synthesis of various commercial products, including polymers, dyes, and plasticizers. For example, they may be readily reduced to form diamines which are useful in the preparation of polyimide resins.

R. L. Markezich and O. S. Zamek disclose (J. Org. Chem. vol. 42, 3431, (1977)) that heating a solution of 4-nitro-N-methylphthalimide with potassium fluoride, potassium nitrite, or sodium nitrite, in solvents such as DMF, dimethyl sulfoxide, or N-methyl pyrrolidone at temperatures of 142°–190° C. produced 4,4'-oxybis(N-methylphthalimide) in yields up to 78%. The authors also disclose that neither potassium fluoride nor potassium nitrite were effective in producing the corresponding diphenyl ether from 4-nitrophthalic anhydride (J. Org. Chem. Vol. 42, 3435 (1977)).

German Patent 2,037,781 (as abstracted in Derwent accession number 72-10017t/07) discloses that para-nitro-benzonitrile forms 4,4'-oxybis(benzonitrile) when reacted with sodium nitrite in a polar organic solvent at a temperature of 100°–220° C.

Japanese patent 80 24125 (as abstracted in Chem. Abstracts 93:167885z) discloses that 1,4-dinitrobenzene may be treated with alkali metal salts or alkali metal hydroxides in polar organic solvents to produce 4,4'-dinitrodiphenyl ether. A similar reaction occurs with 1-cyano-4-nitrobenzene to form 4,4'-dicyanodiphenyl ether.

Japanese patent 78 90230 (as abstracted in Chem. Abstracts 90:22570w) discloses that para-substituted nitro-benzenes react with alkali or alkaline earth metal nitrites in the presence of phase transfer catalysts to form para-substituted diphenyl ethers. The para substituents disclosed are nitro and cyano. In addition, a similar reaction is reported for 1,2-dinitro-4-methylbenzene. In this case, it is the nitro group para to the methyl substituent which is displaced, and not the meta-nitro group and, accordingly, the product is 2,2'-dinitro-4,4'-dimethyl diphenyl ether.

U.S. Pat. No. 4,558,164 discloses a process for the converting ortho or para-nitrochlorobenezene or ortho or para-nitrofluorobenezene into symmetrical dinitrophenyl ethers in a polar organic solvent using a salt of a carboxylic acid, such as benzoic acid or acetic acid as a catalyst and potassium or sodium carbonate as reagents. In the reaction, the halogen atoms of two molecules of the starting material are displaced by oxygen to form the diphenyl ether. The nitro groups are not involved in the condensation.

U.S. Pat. No. 4,933,469 discloses a method for preparing oxybisphthalimides by heating a nitro phthalimide compound in the presence of an alkali metal carboxylate and a phase transfer catalyst in a nonpolar organic solvent. The alkaline metal carboxylate is present in the range from about 0.1 to about 5 moles per mole of nitrophthalimide (10–500 mole percent) and the phase transfer catalyst can be utilized within the range of 2.5 to 30 mole percent. The phase transfer catalyst disclosed are diorganoaminopyridinium salts.

U.S. patent application Ser. No. 594,479, co-pending herewith, discloses that 3,5-dinitrobenzotrifluoride may be reacted, "in an organic solvent in the presence of water and about two equivalents (based on the product weight) of potassium or cesium fluoride" to form 1,1'-oxybis(3-trifluoromethyl-5-nitrobenzene).

SUMMARY OF THE INVENTION

Benzoic acid, substituted benzoic acids, aliphatic carboxylic acids, and alkali metal salts of benzoic and aliphatic carboxylic acids catalyze the condensation, in the presence of an inorganic base, of aromatic nitro compounds to form symmetrical aromatic ethers.

DETAILED DESCRIPTION OF THE INVENTION

Surprisingly, it has now been found that benzoic acid, and substituted benzoic acids, aliphatic carboxylic acids ranging from C2–C14 and alkali metal salts of the listed acids, catalyze the condensation in the presence of an inorganic base, of aromatic nitro compounds of the formula

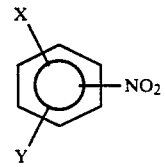

to form symmetrical aromatic ethers of the formula

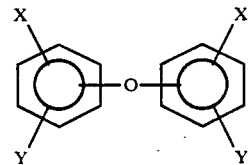

X or Y or both are electron withdrawing groups and may be oriented ortho, meta or para to the nitro group. X and Y may be independently selected and need not be the same. The only requirement for the electron withdrawing group is that it should not undergo side reactions under the reaction conditions. Some groups which are suitable as X and Y substituents are: CN, $CO_2H$, $CO_2R$, CHO, COR, $NO_2$, $NR_3+$, $CF_3$, etc. If X is an extremely strongly electron-withdrawing groups such as nitro, then Y may be a hydrogen. If both X and Y are $CO_2H$ groups these groups may be ortho to one another and exist in the form of an anhydride. Thus, nitrophthalic anhydrides may be condensed to form oxydiphthalic anhydride. Among the nitro aromatic compounds which undergo the carboxylate catalyzed displacement are 1,4-dinitrobenzene, 1,3-dinitrobenzene, 3,5-dinitrobenzotrifluoride, N-methyl-4-nitrophthalimide, 4-nitrobenzonitrile (4NBN), 4-nitrobenzotrifluoride, and 4-nitrophthalic anhydride.

Substituents should not be so bulky as to provide steric inhibition to the displacement of the nitro group and should not react with carboxylates under the reaction conditions. Halogens are not generally suitable substituents because they provide a competitive site where displacement could occur.

The benzoic acid or substituted benzoic acid catalyst is effective at concentrations less than 5 mole % to about 0.1 mole %. Some compounds, such as 3,5-dinitrobenzotrifluoride will condense even in the absence of a catalyst. However, in this case, the presence of catalysts at least doubles the rate of the reaction and thereby makes it more economically feasible. In most cases, such as the condensation of 4-nitrophthalic anhydride, the condensation reaction is difficult in the absence of a catalyst.

The inorganic base may be selected from the alkali metal bicarbonates, carbonates, and hydroxides. The carbonates are generally the preferred bases and preferred carbonate is potassium carbonate.

The condensation may be conducted in dipolar aprotic solvents or in non-polar solvents. If the condensation is conducted in a dipolar aprotic solvent such as dimethyl formamide, dimethyl acetamide, dimethyl sulfoxide, sulfolane, N-methylpyrrolidinone, tetramethylurea, hexamethylphosphoramide, no solubilization agents or phase transfer agents are required. If the condensation is conducted in a non-polar solvent, such as 1,2,4-trichlorobenzene or 1,2-dichlorobenzene, phase transfer agents such as crown ethers, ammonium salts, polyethylene glycol ethers, and phosphonium salts may be required.

The reaction may be run in a temperature range of 80°-220° C. depending on the structure of the nitro compound. In general, the reaction may be run at a lower temperature on compounds in which the electron withdrawing groups are ortho or para to the leaving nitro group than in compounds in which the electron withdrawing group is meta to the leaving nitro group. Thus, the reaction to form an ether from 1,4-dinitrobenzene, using dimethyl sulfoxide as a solvent, may be run at about 90° C., while the same reaction of 1,3-dinitrobenzene requires a temperature of about 160° C.

If the electron withdrawing groups on the substrate molecule include a nitro group, than a second condensation is possible. This condensation occurs after the formation of the ether and involves the displacement of one of the remaining nitro groups by another ether linkage. For example, when 3,5-dinitrobenzotrifluoride is condensed in dimethylacetamide with para-methoxybenzoic acid as a catalyst and potassium carbonate as a base, two products are formed. The first is the dimeric ether, 1,1'-oxybis(3-trifluoromethyl-5-nitrobenzene) (II) and the second is the product of the further condensation, 1,3-di(oxy-3-trifluoromethyl-5-nitrophenyl)5-trifluoromethylbenzene (III)

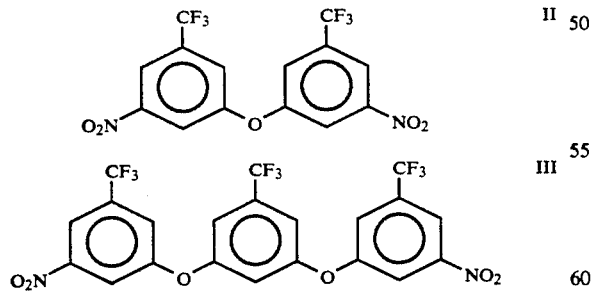

Compound III may be readily reduced, by a wide variety of methods such as formate reduction in the presence of a palladium on charcoal catalyst, hydrogen gas in the presence of a palladium on charcoal catalyst, iron metal and hydrochloric acid, and other methods well known to those skilled in the art. The 1,3-di(oxy-3-trifluoromethyl-5-aminophenyl)-5-trifluoromethylbenzene which is produced is useful in the manufacture of polyimide polymers. These polyimides have desirable electrical properties and are useful for applications such as insulation of wires and other objects, and coating circuit boards. The formation of the polymer is a two step process. In the first step, the dianhydride reacts with the bis ether diamine to form a polyamic acid which generally remains in solution. The polyamic acid solution is then subjected to a curing process which may include heat. If heat is used the solvent evaporates, and the polyamic acid releases water to form the final polyimide. Chemical methods of curing are also available. Among the dianhydrides suitable for the preparation of polyimides from bis ether diamine are: bisphenol S dianhydride, bisphenol A dianhydride, thio-diphthalic anhydride, 4,4'-oxydiphthalic anhydride, symmetrical biphenyl dianhydride, un-symmetrical biphenyl dianhydride, pyromellitic dianhydride, benzophenone tetracarboxylic dianhydride, resorcinol dianhydride, hydroquinone dianhydride. The polyimides formed have the following recurring structure:

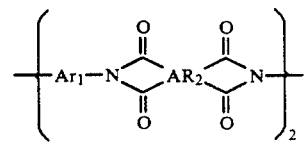

Where AR₂ is

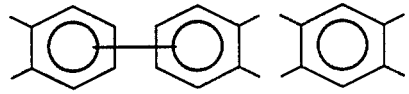

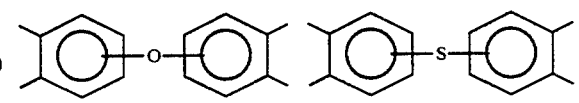

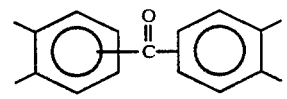

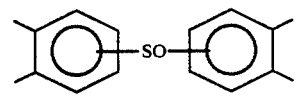

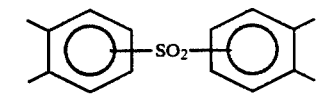

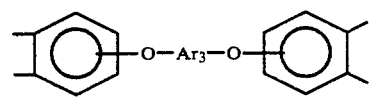

Where AR₃ is

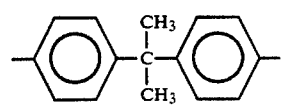

-continued

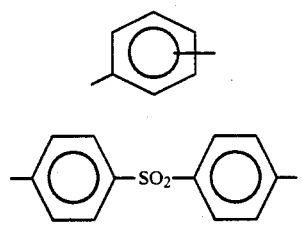

where AR₁ is

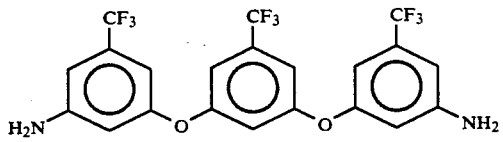

The ethers produced by the process of this invention may readily be isolated by methods which are well known to those skilled in the art. For example, some solvent in which the ether is less soluble, such as water or a non-polar organic solvent may be added to the reaction mixture. This will result in the precipitation of the ether. Alternatively, the solvent may be partially evaporated and mixed with other solvents to cause precipitation of the ether. The invention does not reside in the method of isolating the ether, and obviously isolation and purification methods which will be readily apparent to those skilled in the art may be used with the process of this invention without deviating from the scope or breadth thereof.

EXAMPLES

Example 1

3,5-dinitrobenzotrifluoride (1.0 g) (I), potassium carbonate (0.32 g), and 2 mole % paramethoxybenzoic acid were heated in dimethylacetamide (1.0 mL) for 19 hours. Samples were taken at three times throughout the reaction. Two products were formed 1,1'-oxybis(3-trifluoromethyl-5-nitrobenzene) (II) and 1,3-di(oxy-3-trifluoromethyl-5-nitrophenyl)-5-trifluoromethylbenzene (III).

The percentages of the compounds produced are shown in the chart below. This example is comparable to comparative Example 1.

| 2% paramethoxy-benzoic acid | I | II | III |
|---|---|---|---|
| 1 hr | 92.7% | 7.8% | — |
| 2 hr | 83.5% | 16.5% | — |
| 19 hr | 5.8% | 80.8% | 6.4% |

EXAMPLE 2

4-Nitrobenzonitrile (4-NBN, 0.52 g, 3.54 mmol), potassium carbonate (0.28 g 1.1 eq.) and 3-nitrobenzoic acid (0.0105 g, 0.02 eq.) in N-methylpyrrolidinone (2.0 mL) were heated under nitrogen at 150° C. After 4 hours, the yield of 4,4'-dicyanodiphenylether was 36.9%. Comparative example 1 shows the results of a similar experiment without the 3-nitrobenzoic acid catalyst.

| Reaction with 3-nitrobenzoic acid catalyst: (GC area %) | | | |
|---|---|---|---|
| Time | % 4-NBN | % ether | % 4-HBN |
| 1 hr | 89.9 | 10.1 | 0.0 |
| 2 hr | 77.6 | 19.2 | 3.2 |
| 4 hr | 57.7 | 36.9 | 5.4 |
| 21 hr | 0.0 | 85.5 | 14.5 |

4-NBN = 4-nitrobenzonitrile
ether = 4,4-dicyanodiphenylether
4-HBN = 4-hydroxybenzonitrile

Example 3

1,4-Dinitrobenzene (3.52 g, 20.5 mmol) and potassium carbonate (1.38 g, 10 mmol) were heated in dimethylsulfoxide (8 mL) at about 100° C. for approximately 5.8 hours. The reaction was allowed to cool and was poured into water (20 mL). The reaction vessel was rinsed with an additional 10 mL of water and the rinses were combined. The combined aqueous suspensions were allowed to stand overnight. The solid was collected, washed with water, and dried to give 2.35 g (63% pure) of 4,4'-dinitrodiphenyl ether.

Example 4

1,4-Dinitrobenzene (3.52 g, 20.5 mmol), potassium carbonate (1.38 g, 10 mmol), and sodium 3-nitrobenzoate hemihydrate (32 mg, 0.16 mmol) were heated in dimethylsulfoxide (8 mL) at about 100° C. for approximately 5.8 hours. The reaction was allowed to cool and was poured into water (20 mL). The reaction vessel was rinsed with an additional 10 mL of water and the rinses were combined. The combined aqueous suspensions were allowed to stand overnight. The solid was collected, washed with water, and dried to give 2.51 g (92% pure) of 4,4'-dinitrodiphenyl ether.

Example 5

1,4-Dinitrobenzene (3.52 g, 20.5 mmol), potassium carbonate (1.38 g, 10 mmol), and 4-chlorobenzoic acid (30 mg, 0.19 mmol) were heated in dimethylsulfoxide (8 mL) at about 100° C. for approximately 5.8 hours. The reaction was allowed to cool and was poured into water (20 mL). The reaction vessel was rinsed with an additional 10 mL of water and the rinses were combined. The combined aqueous suspensions were allowed to stand overnight. The solid was collected, washed with water, and dried to give 2.51 g (80% pure) of 4,4'-dinitrodiphenyl ether.

Example 6

1,3-Dinitrobenzene (1,3-DNB, 2.5 g, 15 mmol), potassium carbonate (1.03 g, 7.5 mmol), and N-methyl-2-pyrrolidinone (10 mL) were heated to 150° C. for 1.25 hours. The temperature was raised to 160° C. for one hour and then raised to 170° C. and maintained there for 3.75 hours. The reaction temperature was raised to 180° C. and maintained there for 1 hour. The reaction was monitored by GC and the results are given in the table below.

| | GC Area Percent | |
|---|---|---|
| Time (hrs) | 1,3-DNB | DNE |
| 0.25 | 99.1 | 0 |
| 1.5 | 97.8 | 1.3 |
| 3.5 | 94.3 | 3.2 |
| 5.0 | 89.7 | 5.8 |
| 6.25 | 81.1 | 11.2 |

| | GC Area Percent | |
|---|---|---|
| Time (hrs) | 1,3-DNB | DNE |
| 7.25 | 69.6 | 17.3 |

1,3-DNB = 1,3-dinitrobenzene
DNE = 3,3-dinitrodiphenyl ether

Example 7

1,3-Dinitrobenzene (2.5 g, 15 mmol), potassium Carbonate (1.03 g, 7.5 mmol), 4-chlorobenzoic acid (78 mg, 0.5 mmol), and N-methyl-2-pyrrolidinone (10 mL) were heated to 150° C. for 1.25 hours. The temperature was raised to 160° C. for one hour and then raised to 170° C. and maintained there for 3.75 hours. The reaction temperature was raised to 180° C. and maintained there for 1 hour. The reaction was monitored by GC and the results are given in the table below.

| | GC Area Percent | |
|---|---|---|
| Time (hrs) | 1,3-DNB | DNE |
| 0.25 | 99.5 | 0 |
| 1.5 | 97.3 | 1.5 |
| 3.5 | 94.6 | 3.6 |
| 5.0 | 88.0 | 6.9 |
| 6.25 | 71.9 | 16.2 |
| 7.25 | 51.0 | 26.0 |

Example 8

1,3-Dinitrobenzene (2.5 g, 15 mmol), potassium carbonate (1.03 g, 7.5 mmol), sodium 3-nitrobenzoate hemihydrate (100 mg, 0.5 mmol), and N-methyl-2-pyrrolidinone (10 mL) were heated to 150° C. for 1.25 hours. The temperature was raised to 160° C. for one hour and then raised to 170° C. and maintained there for 3.75 hours. The reaction temperature was raised to 180° C. and maintained there for 1 hour. The reaction was monitored by GC and the results are given in the table below.

| | GC Area Percent | |
|---|---|---|
| Time (hrs) | 1,3-DNB | DNE |
| 0.25 | 100.0 | 0 |
| 1.5 | 100.0 | 0 |
| 3.5 | 91.7 | 4.5 |
| 5.0 | 84.8 | 8.7 |
| 6.25 | 53.2 | 24.1 |
| 7.25 | 17.8 | 41.8 |

Example 9

4-Nitrophthalic anhydride (20.2 g, prepared from 4-nitrophthalic acid obtained from Kodak containing an unknown amount of 3-nitrophthalic anhydride) was heated in 1,2,4-trichlorobenzene to 225° C. (bath temperature). 4-Chlorobenzoic acid (0.06 g) and tetraphenylphosphonium bromide (0.38 g) were added followed by dry potassium carbonate (7.5 g). After heating for 1 hour at 225° C., the temperature of the oil bath was raised to 250° C. and after an additional 1.3 hours more 4-chlorobenzoic acid (0.045 g) was added. The reaction was monitored by GC and the following results obtained.

| Time | Solvent | PAN + 4-CBA | 4-NO2PAN | 3,4'-ODPA | 4,4'-ODPA | Conversion |
|---|---|---|---|---|---|---|
| 1.7 h | 69.3 | 1.7 | 18.2 | 0.2 | 0.3 | 2.7% |
| 2.8 h | 67.4 | 1.6 | 23.1 | 1.48 | 1.20 | 6.5% |
| 3.7 h | 77.9 | 1.8 | 18.0 | 1.82 | 1.88 | 17.1% |
| 5.7 h | 71.6 | 1.9 | 13.8 | 2.34 | 5.42 | 36.0% |

PAN = phthalic anhydride
4-CBA = 4-chlorobenzoic acid
4-NO2PAN = nitrophthalic anhydride
ODPA = oxydiphthalic anhydride

Comparative Example 1

3,5-dinitrobenzotrifluoride (1.0 g) (I) and potassium carbonate (0.32 g) were heated in dimethylacetamide (1.0 mL) for 19 hours. Samples were taken at three times throughout the reaction. Two products were formed 1,1'-oxybis(3-trifluoromethyl-5-nitrobenzene) (II)

and 1,3-di(oxy-3-trifluoromethyl-5-nitrophenyl)-5-trifluoromethylbenzene (III).

The percentages of the compounds produced are shown in the chart below. This example is comparable to example 1.

| NO CATALYST | I | II | III |
|---|---|---|---|
| 1 hr | 95.3% | 4.7% | — |
| 2 hr | 92.8% | 7.1% | — |
| 19 hr | 51.1% | 40.5% | 3.7% |

Comparative Example 2

4-Nitrobenzonitrile (0.52 g, 3.54 mmol), potassium carbonate (0.28 g 1.1 eq.) in N-methylpyrrolidinone (2.0 mL) were heated under nitrogen at 150° C. After 4 hours, the yield of 4,4'-dicyanodiphenylether was 24.9% when the catalyst was omitted. Example 2 shows the results of a similar experiment with the addition of 3-nitrobenzoic acid as a catalyst.

| | Non-catalyzed reaction: (GC area %) | | |
|---|---|---|---|
| Time | % 4-NBN | % ether | % 4-HBN |
| 1 hr | 92.8 | 7.3 | 0.0 |
| 2 hr | 86.9 | 13.1 | 0.0 |
| 4 hr | 69.8 | 24.9 | 5.3 |
| 21 hr | 9.4 | 78.7 | 11.9 |

We claim:

1. A process for the production of diaryl ethers which comprises heating, to a temperature of 80° C. to 220° C., a compound of the formula

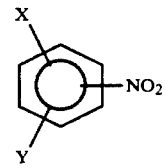

wherein X and Y are selected from the group consisting of H, CN, CO2H, CHO, NO2, and CF3, provided that both X and Y may not simultaneously be H, with the further proviso that if X and Y are ortho to each other and are both CO₂H, they together form an anhydride, in a solvent, in the presence of an inorganic base selected from the group consisting of the alkali metal carbonates, bicarbonates, and hydroxides, and in the presence of a catalyst selected from the group consisting of benzoic acid, substituted benzoic acids, C2–C14 aliphatic carboxylic acids, and alkali metal salts of said acids.

2. A process according to claim 1 wherein X and Y are selected from the group consisting of H, CN, NO₂, CF₃, and CO₂H provided that if X is CO₂H, Y must be CO₂H and X and Y must be ortho to each other and exist in the form of the anhydride.

3. A process for the production of diaryl ethers according to claim 2 in which the inorganic base is sodium carbonate.

4. A process for the production of diaryl ethers according to claim 2 in which the inorganic base is sodium hydroxide.

5. A process for the production of diaryl ethers according to claim 2 in which the inorganic base is potassium carbonate.

6. A process for the production of diaryl ethers according to claim 2 in which the inorganic base is potassium hydroxide.

7. A process for the production of diaryl ethers according to claim 2 in which the solvent is a dipolar aprotic solvent.

8. A process for the production of diaryl ethers according to claim 7 in which the catalyst is selected from the group consisting of benzoic acid and substituted benzoic acids.

9. A process for the production of diaryl ethers according to claim 8 in which the catalyst is benzoic acid.

10. A process for the production of diaryl ethers according to claim 8 in which the catalyst is 3-chlorobenzoic acid.

11. A process for the production of diaryl ethers according to claim 8 in which the catalyst is 4-chlorobenzoic acid.

12. A process for the production of diaryl ethers according to claim 8 in which the catalyst is 3-methylbenzoic acid.

13. A process for the production of diaryl ethers according to claim 8 in which the catalyst is 4-methylbenzoic acid.

14. A process for the production of diaryl ethers according to claim 8 in which the catalyst is 3-methoxybenzoic acid.

15. A process for the production of diaryl ethers according to claim 8 in which the catalyst is 4-methoxybenzoic acid.

16. A process for the production of diaryl ethers according to claim 8 in which the catalyst is 3-nitrobenzoic acid.

17. A process for the production of diaryl ethers according to claim 8 in which the catalyst is 4-nitrobenzoic acid.

18. A process for the production of diaryl ethers according to claim 7 in which the catalyst is selected from the group consisting of C2–C14 aliphatic carboxylic acids.

19. A process for the production of diaryl ethers according to claim 2 in which the catalyst is selected from the group consisting of alkali metal salts of benzoic acid, substituted benzoic acids, and C2–C14 aliphatic carboxylic acids.

20. A process for the production of diaryl ethers according to claim 1 conducted in a non-polar solvent and in the presence of a phase transfer catalyst.

21. A process for the production of diaryl ethers according to claim 19 in which the catalyst is selected from the group consisting of alkali metal salts of benzoic acid and substituted benzoic acids.

22. A process for the production of diaryl ethers according to claim 21 in which the catalyst is an alkali metal salt of benzoic acid.

23. A process for the production of diaryl ethers according to claim 21 in which the catalyst is an alkali metal salt of 3-chlorobenzoic acid.

24. A process for the production of diaryl ethers according to claim 21 in which the catalyst is an alkali metal salt of 4-chlorobenzoic acid.

25. A process for the production of diaryl ethers according to claim 21 in which the catalyst is an alkali metal salt of 3-methylbenzoic acid.

26. A process for the production of diaryl ethers according to claim 21 in which the catalyst is an alkali metal salt of 4-methylbenzoic acid.

27. A process for the production of diaryl ethers according to claim 21 in which the catalyst is an alkali metal salt of 3-methoxybenzoic acid.

28. A process for the production of diaryl ethers according to claim 21 in which the catalyst is an alkali metal salt of 4-methoxybenzoic acid.

29. A process for the production of diaryl ethers according to claim 21 in which the catalyst is an alkali metal salt of 3-nitrobenzoic acid.

30. A process for the production of diaryl ethers according to claim 21 in which the catalyst is an alkali metal salt of 4-nitrobenzoic acid.

31. A process for the production of diaryl ethers according to claim 19 in which the catalyst is selected from the group consisting of C2–C14 aliphatic carboxylic acids.

32. A process for the production of diaryl ethers according to claim 20 in which the catalyst is selected from the group consisting of alkali metal salts of benzoic acid, substituted benzoic acids, and C2–C14 aliphatic carboxylic acids.

* * * * *